(12) United States Patent
Frey et al.

(10) Patent No.: US 7,268,263 B1
(45) Date of Patent: Sep. 11, 2007

(54) INTEGRATED PROCESS FOR AROMATICS PRODUCTION

(75) Inventors: Stanley J. Frey, Palatine, IL (US); Gavin P. Towler, Inverness, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 11/436,443

(22) Filed: May 18, 2006

(51) Int. Cl.
*C07C 6/00* (2006.01)
(52) U.S. Cl. .................. 585/319; 585/323; 585/475
(58) Field of Classification Search ............ 585/319, 585/323, 475
See application file for complete search history.

(56) References Cited

U.S. PATENT DOCUMENTS

| | | | |
|---|---|---|---|
| 3,996,305 A | 12/1976 | Berger | 260/672 T |
| 4,341,914 A | 7/1982 | Berger | 585/474 |
| 4,642,406 A | 2/1987 | Schmidt | 585/477 |
| 5,417,844 A | 5/1995 | Boitiaux et al. | 208/143 |
| 5,658,453 A | 8/1997 | Russ et al. | 208/62 |
| 5,763,720 A | 6/1998 | Buchanan et al. | 585/475 |
| 5,847,256 A | 12/1998 | Ichioka et al. | 585/470 |
| 6,740,788 B1 | 5/2004 | Maher et al. | 585/319 |

OTHER PUBLICATIONS

Robert A. Meyers, *Handbook of Petroleum Refining Processes*, 2d. Edition, 1997, pp. 2.3-2.11.

*Primary Examiner*—Thuan Dinh Dang
(74) *Attorney, Agent, or Firm*—Maryann Maas

(57) ABSTRACT

An aromatics complex flow scheme has been developed. $C_7$-$C_8$ aliphatic hydrocarbons are recycled to an isomerization unit of a xylene recovery zone to increase the efficiency of the isomerization unit. This improvement results in an aromatics complex with savings on capital and utility costs and an improvement on the return on investment.

20 Claims, 1 Drawing Sheet

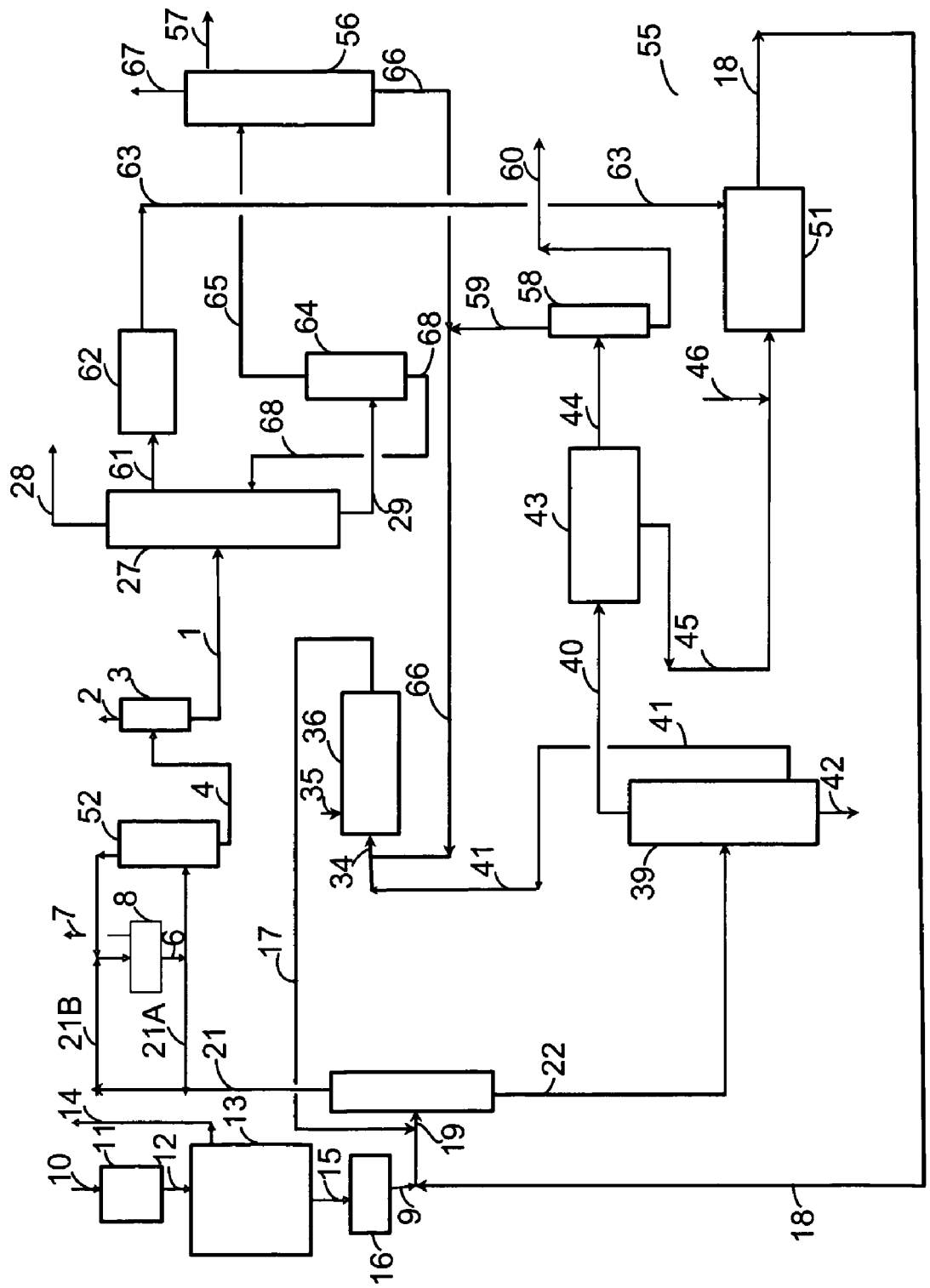

INTEGRATED PROCESS FOR AROMATICS PRODUCTION

FIELD OF THE INVENTION

This invention relates to an aromatics complex flow scheme, which is a combination of process units that can be used to convert naphtha into basic petrochemical intermediates of benzene, toluene, and xylene. Based on a metal catalyzed transalkylation process that handles unextracted toluene and heavier aromatics and an olefin saturation process, the improved flow scheme removes items of equipment and processing steps, such as a deheptanizer column and a toluene column, resulting in significant economic benefits when producing para-xylene. Furthermore, the improved flow scheme improves the efficiency of the isomerization unit through the addition of a stream rich in $C_7$ and $C_8$ aliphatic hydrocarbons.

BACKGROUND OF THE INVENTION

Most new aromatics complexes are designed to maximize the yield of benzene and para-xylene. Benzene is a versatile petrochemical building block used in many different products based on its derivation including ethylbenzene, cumene, and cyclohexane. Para-xylene is also an important building block, which is used almost exclusively for the production of polyester fibers, resins, and films formed via terephthalic acid or dimethyl terephthalate intermediates. Accordingly, an aromatics complex may be configured in many different ways depending on the desired products, available feedstocks, and investment capital available. A wide range of options permits flexibility in varying the product slate balance of benzene and para-xylene to meet downstream processing requirements.

A prior art aromatics complex flow scheme has been disclosed by Meyers in the *Handbook of Petroleum Refining Processes,* 2d. Edition in 1997 by McGraw-Hill.

U.S. Pat. No. 3,996,305 to Berger discloses a fractionation scheme primarily directed to transalkylation of toluene and $C_9$ alkylaromatics in order to produce benzene and xylene. The transalkylation process is also combined with an aromatics extraction process. The fractionation scheme includes a single column with two streams entering and with three streams exiting the column for integrated economic benefits.

U.S. Pat. No. 4,341,914 to Berger discloses a transalkylation process with recycle of $C_{10}$ alkylaromatics in order to increase yield of xylenes from the process. The transalkylation process is also preferably integrated with a para-xylene separation zone and a xylene isomerization zone operated as a continuous loop receiving mixed xylenes from the transalkylation zone feedstock and effluent fractionation zones.

U.S. Pat. No. 4,642,406 to Schmidt discloses a high severity process for xylene production that employs a transalkylation zone that simultaneously performs as an isomerization zone over a nonmetal catalyst. High quality benzene is produced along with a mixture of xylenes, which allows para-xylene to be separated by absorptive separation from the mixture with the isomer-depleted stream being passed back to the transalkylation zone.

U.S. Pat. No. 5,417,844 to Boitiaux et al. discloses a process for the selective dehydrogenation of olefins in steam cracking petrol in the presence of a nickel catalyst and is characterized in that prior to the use of the catalyst, a sulfur-containing organic compound is incorporated into the catalyst outside of the reactor prior to use.

U.S. Pat. No. 5,658,453 to Russ et al. discloses an integrated reforming and olefin saturation process. The olefin saturation reaction uses a mixed vapor phase with addition of hydrogen gas to a reformate liquid in contact with a refractory inorganic oxide containing preferably a platinum-group metal and optionally a metal modifier.

U.S. Pat. No. 5,763,720 to Buchanan et al. discloses a transalkylation process for producing benzene and xylenes by contacting a $C_9^+$ alkylaromatics with benzene and/or toluene over a catalyst comprising a zeolite such as ZSM-12 and a hydrogenation noble metal such as platinum. Sulfur or stream is used to treat the catalyst.

U.S. Pat. No. 5,847,256 to Ichioka et al. discloses a process for producing xylene from a feedstock containing $C_9$ alkylaromatics with the aid of a catalyst with a zeolite that is preferably mordenite and with a metal that is preferably rhenium.

U.S. Pat. No. 6,740,788 discloses an aromatics complex flow scheme which, as compared to a traditional complex, removes items of equipment and processing steps such as a reformate splitter column and a heavy aromatics column.

The present invention provides an aromatics complex flow scheme arranged and operated so that a traditional deheptanizer column in the xylenes recovery section may be eliminated. With this invention, capital costs are reduced, operating costs are reduced, and the yield of $C_8$ aromatics is improved. Furthermore, the efficiency of the isomerization unit is increase through the addition of a stream rich in $C_7$ and $C_8$ aliphatic hydrocarbons. A traditional toluene column is also eliminated thereby saving additional costs.

SUMMARY OF THE INVENTION

An aromatics complex flow scheme having a transalkylation stripper fractionation zone operated so that toluene and lighter materials are removed in an overhead which allows for the recycle of an entire isomerization unit effluent to the transalkylation stripper fractionation zone without passing the effluent though a deheptanizer column. Introducing a stream rich in $C_7$ and $C_8$ aliphatic hydrocarbons to the isomerization unit allows the unit to operate more efficiently and at a lower temperature. Some of the aliphatic hydrocarbons are converted to lighter aliphatic hydrocarbons, but the presence of the aliphatic hydrocarbons in the isomerization unit allows the reaction to proceed more rapidly and allows the unit to be operated at a lower temperature thereby increasing the overall yield of the process. $C_8$ aliphatic hydrocarbons do not build up in the xylenes recovery zone since they are removed in the transalkylation stripper fractionation zone. Also, by using both $C_9$ and $C_{10}$ alkylaromatics in an enabled transalkylation unit, the flow scheme further omits a heavy aromatics column. Another enhancement to the flow scheme is accomplished through the elimination of clay treaters in favor of selective olefin saturation at the exits of a reforming process unit or of an alkylaromatic isomerization process unit. Another embodiment of the present invention comprises an apparatus that is based on the process steps, which efficiently converts naphtha into para-xylene.

BRIEF DESCRIPTION OF THE DRAWING

The Figure shows an aromatics complex flow scheme of the present invention, which includes operating the transalkylation stripper fractionation zone to generate an overhead stream containing toluene and lighter components. A stream rich in $C_7$ and $C_8$ aliphatic hydrocarbons separated from the transalkylation stripper fractionation zone overhead is recycled to the isomerization unit. The aromatics complex of the present invention does not include a deheptanizer column.

DETAILED DESCRIPTION OF THE INVENTION

Feed to the complex may be naphtha, but can also be pygas, imported mixed xylene, or imported toluene. Naphtha fed to an aromatics complex is first hydrotreated to remove sulfur and nitrogen compounds to less than about 0.5 wt-ppm before passing the treated naphtha on to a reforming unit 13. Naphtha hydrotreating occurs by contacting naphtha in a line 10 with a naphtha hydrotreating catalyst under naphtha hydrotreating conditions in a unit 11. The naphtha hydrotreating catalyst is typically composed of a first component of cobalt oxide or nickel oxide, along with a second component of molybdenum oxide or tungsten oxide, and a third component inorganic oxide support, which is typically a high purity alumina. Generally good results are achieved when the cobalt oxide or nickel oxide component is in the range of about 1 to about 5 wt-% and the molybdenum oxide component is in the range of about 6 to about 25 wt-%. The alumina (or aluminum oxide) is set to balance the composition of the naphtha hydrotreating catalyst to sum all components up to 100 wt-%. One hydrotreating catalyst for use in the present invention is disclosed in U.S. Pat. No. 5,723,710, the teachings of which are incorporated herein by reference. Typical hydrotreating conditions include a liquid hourly space velocity (LHSV) from about 1.0 to about 5.0 $hr^{-1}$, a ratio of hydrogen to hydrocarbon (or naphtha feedstock) from about 50 to about 135 $Nm^3/m^3$, and a pressure from about 10 to about 35 $kg/cm^2$.

In the reforming unit 13, paraffins and naphthenes are converted to aromatics. This is the only unit in the complex that actually creates aromatic rings. The other units in the complex separate the various aromatic components into individual products and convert various aromatic species into higher-value products. The reforming unit 13 is usually designed to run at very high severity, equivalent to producing about 100 to about 106 Research Octane Number (RONC) gasoline reformate, in order to maximize the production of aromatics. This high severity operation yields very low non-aromatic impurities in the $C_8^+$ fraction of reformate, and eliminates the need for extraction of the $C_8$ and $C_9$ aromatics.

In the reforming unit 13, hydrotreated naphtha from a line 12 is contacted with a reforming catalyst under reforming conditions. The reforming catalyst is typically composed of a first component platinum-group metal, a second component modifier metal, and a third component inorganic-oxide support, which is typically high purity alumina. Generally good results are achieved when the platinum-group metal is in the range of about 0.01 to about 2.0 wt-% and the modifier metal component is in the range of about 0.01 to about 5 wt-%. The alumina is set to balance the composition of the naphtha hydrotreating catalyst to sum all components up to 100 wt-%. The platinum-group metal is selected from platinum, palladium, rhodium, ruthenium, osmium, and iridium. The preferred platinum-group metal component is platinum. The metal modifiers may include rhenium, tin, germanium, lead, cobalt, nickel, indium, gallium, zinc, uranium, dysprosium, thallium, and mixtures thereof. One reforming catalyst for use in the present invention is disclosed in U.S. Pat. No. 5,665,223, the teachings of which are incorporated herein by reference. Typical reforming conditions include a liquid hourly space velocity from about 1.0 to about 5.0 $hr^{-1}$, a ratio of hydrogen to hydrocarbon from about 1 to about 10 moles of hydrogen per mole of hydrocarbon feed entering the reforming zone, and a pressure from about 2.5 to about 35 $kg/cm^2$. Hydrogen produced in the reforming unit 13 exits in a line 14.

The olefin saturation zone 16 may consist of the well-known clay treating means or other means to treat residual olefin contaminants. Preferably, the olefin saturation zone 16 comprises an olefin saturation catalyst operating under olefin saturation conditions. Catalytic olefin saturation is also a flow scheme enabler. If a catalytic process is used, the olefins are converted to useful products. For example, a $C_6$ olefin can be converted to benzene (if the olefin is cyclic), a $C_7$ to toluene, and a $C_8$ to xylene. If clay is used, then the olefin will be polymerized, often to $C_{11}^+$, which is not very useful for an aromatics complex. Thus, the catalytic olefin saturation helps improve the economics of the flow scheme. Suitable olefin saturation catalysts in the present invention contain elemental nickel or a platinum-group component preferably supported on an inorganic oxide support, which is typically alumina. In the case where the elemental nickel is present on a support, the nickel is preferably present in an amount from about 2 to about 40 wt-% of the total catalyst weight. One catalyst for use in the present invention is disclosed in U.S. Pat. No. 5,658,453, the teachings of which are incorporated herein by reference. Typical olefin saturation conditions include a temperature from about 20° to about 200° C., a pressure from about 5 to about 70 $kg/cm^2$ and a stoichiometric ratio of hydrogen to olefins from about 1:1 to about 5:1. Olefin treated reformate is shown in a line 9.

The reformate comprising aromatics, non-aromatics, and light ends in a line 9 is combined with a transalkylation unit effluent in line 17 and an ethylbenzene dealkylation and isomerization unit effluent in a line 18 and sent to a transalkylation stripper fractionation zone 54 via a line 19. The transalkylation stripper fractionation zone 54 generally comprises at least one fractionation column. The transalkylation stripper fractionation zone 54 produces a toluene and lighter fraction which contains toluene and benzene, and lighter hydrocarbons including $C_8$, $C_7$, and lighter aliphatic hydrocarbons in a line 21 and a xylenes-plus-enriched fraction which contains xylenes, heavier aromatics and $C_9$ and heavier aliphatic hydrocarbons in a line 22. The xylene-plus-enriched stream in line 22 from the bottom of the transalkylation stripper fractionation zone 54 is sent to a xylene recovery section 55 (described below) of the aromatics complex.

A portion 21B of the toluene and lighter hydrocarbon stream in line 21 is sent to a common overhead receiver 8 from which light gases such as hydrogen, methane and ethane is removed and directed to, for example, fuel gas. Overhead receiver bottoms stream 6 is combined with the remainder of the toluene and lighter hydrocarbon stream in line 21A and passed to stripper column 52. In stripper column 52, light gasses such as hydrogen, methane, and ethane are removed in a stripper overhead stream 5 and directed to common overhead receiver 8. Additional hydrocarbons may be carried with the light gasses. The Figure shows one embodiment of the invention, and an alternative embodiment would be for transalkylation stripper fractionation zone 54 and stripper column 52 to each have independent overhead receivers instead of the common overhead receiver 8. Stripper bottoms stream 4 containing the reminder of the toluene and lighter hydrocarbon stream is passed to stabilizer 3. Stabilizer 3 produces LPG, primarily propane and butane, which is removed in a line 2. The remainder containing toluene and lighter hydrocarbons through pentane are removed from the stabilizer 3 in a stabilizer bottoms stream 1. Stabilizer bottoms stream 1 is conducted to aromatic extraction zone 27 which produces a benzene and toluene product stream in a line 29; rejects a by-product raffinate stream in a line 28; and produces a $C_7$-$C_8$ aliphatic stream in line 61. The raffinate stream comprising contaminates that are lighter than or co-boiling with benzene may be blended into gasoline, used as feedstock for an ethylene plant, or converted into additional benzene by recycling to the reforming unit 13. The use of extractive distillation instead of liquid-liquid extraction or combined liquid-liquid extraction/extractive distillation processes may result in an economic improvement. However, liquid-liquid extraction is a suitable alternative.

Extractive distillation is a technique for separating mixtures of components having nearly equal volatility and having nearly the same boiling point. It is difficult to separate the components of such mixtures by conventional fractional distillation. In extractive distillation, a solvent is introduced into a main distillation column above the entry point of the hydrocarbon-containing fluid mixture that is to be separated. The solvent affects the volatility of the hydrocarbon-containing fluid component boiling at a higher temperature differently than the hydrocarbon-containing fluid component boiling at a lower temperature sufficiently to facilitate the separation of the various hydrocarbon-containing fluid components by distillation and such solvent exits with the bottoms fraction. Suitable solvents include tetrahydrothiophene 1,1-dioxide (or sulfolane), diethylene glycol, triethylene glycol, or tetraethylene glycol. The raffinate stream in line 28 comprising nonaromatic compounds exits overhead of the main distillation column, while the bottoms fraction containing solvent and benzene exits below. Often the raffinate will be sent to a wash column (not shown) in order to be contacted with a wash fluid such as water and thus remove any residual dissolved solvent. The side-cut $C_7$-$C_8$ aliphatic hydrocarbon stream in line 61 may be passed through a trace solvent removal zone 62 in order to remove residual dissolved solvent. The substantially solvent free stream in line 63 is introduced to isomerization unit 63, discussed in detail below. The substantially solvent free stream contains no more than about 10 ppm solvent and preferably no more than about 1 ppm solvent. In one embodiment of the invention the trace solvent removal zone 62 is a wash column and in another embodiment of the invention the trace solvent removal zone 62 is a water wash column.

In an alternate embodiment, the extractive distillation zone may contain two or more columns with a main extractive distillation column as described above and one or more fractional distillation columns. In this embodiment, the overhead from the extractive distillation column would contain the non-aromatic hydrocarbons including the $C_7$-$C_8$ aliphatic hydrocarbons that were removed in a side-cut stream in the embodiment described in the previous paragraph. A solvent removal unit (not shown) may be used to separate and recycle any solvent in the overhead stream. Then a fractional distillation column (not shown) would be used to separate at least some of the $C_7$-$C_8$ aliphatic hydrocarbons from other non-aromatic hydrocarbons and the separated $C_7$-$C_8$ aliphatic hydrocarbons would be conducted to an isomerization zone as discussed below.

The bottoms stream 29 from the main distillation column 27 is sent to a solvent recovery column 64, where benzene and toluene is recovered overhead 65 and the solvent is recovered from the bottom 68 and passed back to the main distillation column 27. The recovery of high purity benzene and toluene in the line 65 from extractive-distillation and solvent recovery typically exceeds 99 wt-%. Water may be removed from the high purity benzene in line 65 using a benzene dryer column 56 to produce a dry benzene product stream 57. Water is removed from benzene dryer column 56 in line 67. Toluene is also separated from benzene in benzene dryer column 56. The toluene is removed in line 66 and is passed to a transalkylation zone 36. Before being introduced into transalkylation zone 36, the toluene in line 66 is usually blended with a stream in a line 41 rich in $C_9$ and $C_{10}$ alkylaromatics produced by a xylene column 39 and charged via a line 34 to the transalkylation zone 36 for production of additional xylenes and benzene.

In the transalkylation zone 36, the feed is contacted with a transalkylation catalyst under transalkylation conditions. The preferred catalyst is a metal stabilized transalkylation catalyst. Such catalyst comprises a zeolite component, a metal component, and an inorganic oxide component. The zeolite component typically is either a pentasil zeolite, which include the structures of MFI, MEL, MTW, MTT and FER (IUPAC Commission on Zeolite Nomenclature), a beta zeolite, or a mordenite. Preferably it is mordenite zeolite. The metal component typically is a noble metal or base metal. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Preferably the metal component comprises rhenium. Suitable metal amounts in the transalkylation catalyst range from about 0.01 to about 10 wt-%, with the range from about 0.1 to about 3 wt-% being preferred, and the range from about 0.1 to about 1 wt-% being highly preferred. Suitable zeolite amounts in the catalyst range from about 1 to about 99 wt-%, preferably between about 10 to about 90 wt-%, and more preferably between about 25 to about 75 wt-%. The balance of the catalyst is composed of inorganic oxide binder, preferably alumina. One transalkylation catalyst for use in the present invention is disclosed in U.S. Pat. No. 5,847,256, which is hereby incorporated by reference.

Conditions employed in the transalkylation zone normally include a temperature of from about 200° to about 540° C. The transalkylation zone is operated at moderately elevated pressures broadly ranging from about 1 to about 60 kg/cm². The transalkylation reaction can be effected over a wide range of space velocities, with higher space velocities effecting a higher ratio of para-xylene at the expense of conversion. Liquid hourly space velocity generally is in the range of from about 0.1 to about 20 hr$^{-1}$ The feedstock is preferably transalkylated in the vapor phase and in the presence of hydrogen supplied via a line 35. If transalkylated in the liquid phase, then the presence of hydrogen is optional. If present, free hydrogen is associated with the feedstock and recycled hydrocarbons in an amount of about 0.1 moles per mole of alkylaromatics up to about 10 moles per mole of alkylaromatic. This ratio of hydrogen to alkylaromatic is also referred to as hydrogen to hydrocarbon ratio.

The effluent from the transalkylation zone 36 is sent to the transalkylation stripper fractionation zone 54 through the lines 17 followed by 19. There the toluene and lighter hydrocarbons are recovered in the overhead 21 with the benzene being recovered as product and the toluene ultimately conducted to the transalkylation zone 36 as discussed above. The xylenes and heavier hydrocarbons are fractionated out into the xylenes-plus-enriched stream 22 and are sent to the xylene recovery section 55.

The xylene recovery section 55 of the aromatics complex comprises at least one xylene column 39, and generally will further include a process unit for separation of at least one xylene isomer, which is typically the para-xylene product from the aromatics complex. Preferably such a para-xylene separation zone 43 is operated in conjunction with an isomerization unit 51 for isomerization of the remaining alkylaromatic compounds back to an equilibrium or near equilibrium mixture containing para-xylene, which can be recycled for further recovery in a loop-wise fashion. Accordingly, the xylene-plus-enriched stream in line 22 is charged to a xylene column 39. The xylene column 39 is designed to rerun a feed stream in a line 40 to the para-xylene separation zone 43 down to very low levels of $C_9$ alkylaromatics ($A_9$) concentration. $A_9$ compounds may build up in a desorbent circulation loop within the para-xylene separation zone 43, so it is more efficient to remove this material upstream in the xylene column 39. The overhead feed stream in the line 40 from the xylene column 39 is charged directly to the para-xylene separation zone 43.

Material from the lower part of the xylene column 39 is withdrawn as a stream rich in $C_9$ and $C_{10}$ alkylaromatics via the line 41, which is then sent to the transalkylation zone 36 for production of additional xylenes and benzene. The stream in line 41 taken as a sidecut stream on the xylene column (which eliminates a heavy aromatics column) is enabled by the metal stabilized transalkylation catalyst. A separate column doing a rigorous split to keep coke precursors such as methyl indan or naphthalene out of the stream is no longer needed because the metal stabilized transalkylation catalyst is not materially effected by those components. Any remaining $C_{11}^+$ material is rejected from the bottom of the xylene column 39 via a line 42. Another embodiment is to send an entire xylene column bottoms stream to the transalkylation zone instead of only a sidecut stream.

Alternatively, if ortho-xylene is to be produced in the complex, the xylene column is designed to make a split between meta- and ortho-xylene and drop a targeted amount of ortho-xylene to the bottoms. The xylene column bottoms are then sent to an ortho-xylene column (not shown) where high purity ortho-xylene product is recovered overhead. Material from the lower part of the ortho-xylene column is withdrawn as a stream rich in $C_9$ and $C_{10}$ alkylaromatics then sent to transalkylation zone 36. Any remaining $C_{11}^+$ material is rejected from the bottom of the ortho-xylene column.

The para-xylene separation zone 43 may be based on a fractional crystallization process or an adsorptive separation process, both of which are well known in the art, and preferably is based on the adsorptive separation process. Such adsorptive separation can recover over highly pure para-xylene in a line 44 at high recovery per pass. Any residual toluene in the feed to the separation unit is extracted along with the para-xylene, fractionated out in a finishing column 58 within the unit, and then optionally recycled to the transalkylation zone stripper column 52 in line 59. Having finishing column 58 allows for optimization and flexibility in operating the xylenes column 39 since any toluene in the overhead from the xylene column would be removed from the para-xylene product and recycled to the transalkylation zone. Very high purity para-xylene product, over 99 wt-% pure para-xylene, is removed from the process in line 60.

The raffinate from the para-xylene separation zone 43 is almost entirely depleted of para-xylene, to a level usually of less than 1 wt-%. The raffinate is sent via a line 45 to the alkylaromatics isomerization unit 51, where additional para-xylene is produced by reestablishing an equilibrium or near-equilibrium distribution of xylene isomers. Any ethyl benzene in the para-xylene separation unit raffinate is either converted to additional xylenes, transalkylated to a $C_9$ aromatic, or converted to benzene by dealkylation, depending upon the type of isomerization catalyst used. As discussed above, a stream of $C_7$-$C_8$ aliphatic hydrocarbons is also introduced into isomerization unit 51. Since $C_7$ and $C_8$ aliphatic hydrocarbons are intermediates in the conversion of ethyl benzene to xylenes, the presence of the $C_7$-$C_8$ aliphatic hydrocarbons in the reaction mixture allows for the conversion of any ethyl benzene to xylene to happen more rapidly. The $C_7$-$C_8$ aliphatic hydrocarbons further allow for the unit to be successfully operated at a lower temperature.

In the alkylaromatic isomerization unit 51, the raffinate stream in line 45 is contacted with an isomerization catalyst under isomerization conditions. The isomerization catalyst is typically composed of a molecular sieve component, a metal component, and an inorganic oxide component. Selection of the molecular sieve component allows control over the catalyst performance between ethylbenzene isomerization and ethylbenzene dealkylation depending on overall demand for benzene. Consequently, the molecular sieve may be either a zeolitic aluminosilicate or a non-zeolitic molecular sieve. The zeolitic aluminosilicate (or zeolite) component typically is either a pentasil zeolite, which include the structures of MFI, MEL, MTW, MTT and FER (IUPAC Commission on Zeolite Nomenclature), a beta zeolite, or a mordenite. The non-zeolitic molecular sieve is typically one or more of the AEL framework types, especially SAPO-11, or one or more of the ATO framework types, especially MAPSO-31, according to the "Atlas of Zeolite Structure Types" (Butterworth-Heineman, Boston, Mass., 3rd ed. 1992). The metal component typically is a noble metal component, and may include an optional base metal modifier component in addition to the noble metal or in place of the noble metal. The noble metal is a platinum-group metal is selected from platinum, palladium, rhodium, ruthenium, osmium, and iridium. The base metal is selected from the group consisting of rhenium, tin, germanium, lead, cobalt, nickel, indium, gallium, zinc, uranium, dysprosium, thallium, and mixtures thereof. The base metal may be combined with another base metal, or with a noble metal. Suitable total metal amounts in the isomerization catalyst range from about 0.01 to about 10 wt-%, with the range from about 0.1 to about 3 wt-% preferred. Suitable zeolite amounts in the catalyst range from about 1 to about 99 wt-%, preferably between about 10 to about 90 wt-%, and more preferably between about 25 to about 75 wt-%. The balance of the catalyst is composed of inorganic oxide binder, typically alumina. One isomerization catalyst for use in the present invention is disclosed in U.S. Pat. No. 4,899,012, the teachings of which are incorporated herein by reference.

Typical isomerization conditions include a temperature in the range from about 0° to about 600° C. and a pressure from atmospheric to about 50 kg/cm². The liquid hourly hydrocarbon space velocity of the feedstock relative to the volume of catalyst is from about 0.1 to about 30 hr$^{-1}$. The hydrocarbon contacts the catalyst in admixture with a gaseous hydrogen-containing stream in a line 46 at a hydrogen-tohydrocarbon mole ratio of from about 0.5:1 to 15:1 or more, and preferably a ratio of from about 0.5 to 10. If liquid phase conditions are used for isomerization, then no hydrogen is added to the unit.

The effluent from the isomerization unit 51 containing at least a mixture of xylenes is sent via a line 18 to the transalkylation stripper fractionation zone 54. There is no need for a traditional deheptanizer column between the isomerization unit and the transalkylation stripper fractionation zone, the entire effluent of the isomerization unit may be passed to the transalkylation stripper fractionation zone 54 thereby saving substantial capital costs and ongoing utilities costs. The $C_7$-minus hydrocarbons that would have been removed from the xylenes in an overhead of a deheptanizer column are instead passed to the transalkylation stripper fractionation zone 54 and separated from the xylenes there.

Accordingly, the aromatics complex of the present invention displays excellent economic benefits. These improvements result in an aromatics complex with savings in capital costs and operating costs, and an improvement on the return on investment in such a complex.

What is claimed is:

1. A process for isomerizing xylenes comprising:
   (a) providing a naphtha stream to a hydrotreating zone, wherein the naphtha stream is contacted with a hydrotreating catalyst under hydrotreating conditions to produce a hydrotreated naphtha stream;
   (b) passing the hydrotreated naphtha stream to a reforming zone, wherein said hydrotreated naphtha is contacted with a reforming catalyst under reforming conditions to produce a reformate stream comprising aromatic components and light-end hydrocarbons;
   (c) introducing all of the reformate stream, a transalkylation product stream, and an isomerization zone effluent, in individual streams or a combined stream, to a transalkylation stripper zone and separating a toluene and lighter hydrocarbons enriched stream and a xylene and heavier hydrocarbons enriched stream; and
   (d) removing light ends and LPG from the toluene and lighter hydrocarbons enriched stream to form a feed stream comprising benzene, toluene, and $C_5$-$C_8$ aliphatic hydrocarbons;
   (e) introducing the feed stream comprising benzene, toluene, and $C_5$-$C_8$ aliphatic hydrocarbons into an extractive distillation zone to separate a bottoms aromatic hydrocarbons stream comprising benzene and toluene, a sidecut aliphatic hydrocarbons stream comprising $C_7$-$C_8$ aliphatic hydrocarbons, and an overhead aliphatic hydrocarbons stream comprising $C_5$-$C_7$ aliphatic hydrocarbons;
   (f) treating the sidecut aliphatic hydrocarbons stream comprising $C_7$-$C_8$ aliphatic hydrocarbons to generate a substantially solvent-free sidecut aliphatic hydrocarbons stream;
   (g) introducing the substantially solvent-free sidecut aliphatic hydrocarbons stream comprising $C_7$-$C_8$ aliphatic hydrocarbons, hydrogen, and a non-equilibrium xylene stream comprising a non-equilibrium mixture of xylenes into an isomerization zone to contact an isomerization catalyst at isomerization conditions and generate the isomerization zone effluent.

2. The process of claim 1 wherein the isomerization catalyst comprises a molecular sieve component, a metal component, and an inorganic oxide component.

3. The process of claim 1 wherein the isomerization conditions comprises a temperature in the range from about 0° to about 600° C., a pressure from atmospheric to about 50 kg/cm², and a liquid hourly hydrocarbon space velocity from about 0.1 to about 30 hr$^{-1}$.

4. The process of claim 1 further comprising passing the bottoms aromatic hydrocarbons stream comprising benzene and toluene to a fractionation column to separate a benzene-enriched stream and a toluene-enriched stream.

5. The process of claim 4 further comprising passing the toluene-enriched stream to a transalkylation zone.

6. The process of claim 1 further comprising passing the reformate stream through an olefin saturation unit prior to combining with the transalkylation product stream and the isomerization zone effluent stream.

7. The process of claim 6 wherein the olefin saturation catalyst comprises a nickel or a platinum-group component, and an inorganic oxide component and the olefin saturation conditions comprise a temperature from about 20° to about 200° C., a pressure from about 5 to about 70 kg/cm² and a stoichiometric ratio of hydrogen to olefins from about 1:1 to about 5:1.

8. The process of claim 1 wherein the hydrotreating catalyst comprises a component of cobalt oxide or nickel oxide, a component of molybdenum oxide or tungsten oxide, and a component of inorganic oxide support.

9. The process of claim 1 wherein the hydrotreating conditions comprise a liquid hourly space velocity from about 1.0 to about 5.0 hr$^{-1}$, a ratio of hydrogen to naphtha feedstock from about 50 to about 135 Nm³/m³, and a pressure from about 10 to about 35 kg/cm².

10. The process of claim 1 wherein the reforming catalyst comprises a first component platinum-group metal, a second component modifier metal, and a third component inorganic-oxide support.

11. The process of claim 1 wherein the reforming conditions comprise a liquid hourly space velocity from about 1.0 to about 5.0 hr$^{-1}$, a ratio of hydrogen to hydrocarbon from about 1 to about 10 moles of hydrogen per mole of naphtha, and a pressure from about 2.5 to about 35 kg/cm².

12. The process of claim 1 further comprising:
   (h) separating the xylene and heavier hydrocarbons enriched stream in a xylene fractionation zone to produce an overhead xylene stream and a stream rich in $C_9$ and $C_{10}$ alkylaromatic hydrocarbons;
   (i) passing the toluene-enriched stream and the stream rich in $C_9$ and $C_{10}$ alkylaromatic hydrocarbons, or the combination thereof, to a transalkylation zone wherein said streams are contacted with a metal-stabilized transalkylation catalyst under transalkylation conditions to produce the transalkylation product stream of claim 1(c); and
   (j) passing the overhead xylene stream to a para-xylene separation zone to concentrate and remove a para-xylene enriched product stream and generate the non-equilibrium xylene stream of claim 1(g).

13. The process of claim 12 wherein the metal-stabilized transalkylation catalyst comprises a zeolite component, a metal component, and an inorganic oxide component.

14. The process of claim 12 wherein the metal component is selected from the group consisting of platinum, palladium, rhodium, ruthenium, osmium, and iridium, rhenium, tin, germanium, lead, cobalt, nickel, indium, gallium, zinc, uranium, dysprosium, thallium, and mixtures thereof.

15. The process of claim 12 wherein the zeolite component is selected from the group consisting of a pentasil zeolite, a beta zeolite, a mordenite zeolite, or mixtures thereof.

16. The process of claim 12 wherein the transalkylation conditions comprise a temperature from about 200° to about 540° C., a pressure from about 1 to about 60 kg/cm$^2$, and a liquid hourly space velocity from about 0.1 to about 20 hr$^-$.

17. The process of claim 12 further comprising separating, in the xylene fractionation zone, a bottoms stream rich in C$_{11}$ alkylaromatics which is removed from the process.

18. A process for producing benzene and para-xylene from a naphtha feedstock comprising the steps of:
(a) providing a naphtha feed feedstock stream to a hydrotreating zone, wherein the feedstock is contacted with a hydrotreating catalyst under hydrotreating conditions to produce a hydrotreated naphtha stream; and
(b) passing the hydrotreated naphtha stream to a reforming zone, wherein said hydrotreated naphtha is contacted with a reforming catalyst under reforming conditions to produce a reformate stream comprising aromatic components and light-end hydrocarbons;
(c) separating all of the reformate stream, a transalkylation product stream, and an isomerization product stream, in individual streams or a combined stream, in a transalkylation stripper zone to produce a toluene and lighter hydrocarbons enriched stream and a xylene and heavier hydrocarbons enriched stream;
(d) passing the toluene and lighter hydrocarbons enriched stream to an extractive-distillation zone to produce a raffinate stream, a stream containing C$_7$-C$_8$ aliphatic hydrocarbons, and a benzene and toluene enriched stream;
(e) separating the benzene and toluene enriched stream in a fractionation column to produce a benzene-enriched stream and a toluene-enriched stream;
(f) separating the xylene and heavier hydrocarbons enriched stream of step (c) in a xylene fractionation zone to produce a xylene-enriched stream and a stream rich in C$_9$ and C$_{10}$ alkylaromatic hydrocarbons;
(g) passing the toluene-enriched stream and the stream rich in C$_9$ and C$_{10}$ alkylaromatic hydrocarbons, or a combined stream thereof, to a transalkylation zone, wherein said streams are contacted with a metal-stabilized transalkylation catalyst under transalkylation conditions to produce the transalkylation product stream of step (c);
(h) passing the xylene-enriched stream to a para-xylene separation zone, wherein para-xylene is concentrated into a para-xylene enriched product stream and a para-xylene separation zone effluent stream; and
(i) passing the para-xylene separation zone effluent stream to a xylenes isomerization zone wherein said stream is contacted with an isomerization catalyst under isomerization conditions to produce the isomerization product stream of step (c).

19. A process for isomerizing xylenes comprising:
(a) providing a naphtha stream to a hydrotreating zone, wherein the naphtha stream is contacted with a hydrotreating catalyst under hydrotreating conditions to produce a hydrotreated naphtha stream;
(b) passing the hydrotreated naphtha stream to a reforming zone, wherein said hydrotreated naphtha is contacted with a reforming catalyst under reforming conditions to produce a reformate stream comprising aromatic components and light-end hydrocarbons;
(c) introducing all of the reformate stream, a transalkylation product stream, and an isomerization zone effluent, in individual streams or a combined stream, to a transalkylation stripper zone and separating a toluene and lighter hydrocarbons enriched stream and a xylene and heavier hydrocarbons enriched stream; and
(d) removing light ends and LPG from the toluene and lighter hydrocarbon enriched stream to form a feed stream comprising benzene, toluene, and C$_5$-C$_8$ aliphatic hydrocarbons;
(e) introducing the feed stream comprising benzene, toluene, and C$_5$-C$_8$ aliphatic hydrocarbons into an extractive distillation zone to separate a bottoms aromatic hydrocarbons stream comprising benzene and toluene, and an overhead aliphatic hydrocarbons stream comprising C$_5$-C$_8$ aliphatic hydrocarbons;
(f) treating the overhead aliphatic hydrocarbons stream comprising C$_5$-C$_8$ aliphatic hydrocarbons to generate a substantially solvent-free aliphatic hydrocarbons stream;
(g) separating the substantially solvent-free aliphatic hydrocarbons stream into a C$_5$-C$_7$ aliphatic hydrocarbon stream and a C$_7$-C$_8$ aliphatic hydrocarbon stream;
(h) introducing the C$_7$-C$_8$ aliphatic hydrocarbons, hydrogen, and a non-equilibrium xylene stream comprising a non-equilibrium mixture of xylenes into an isomerization zone to contact an isomerization catalyst at isomerization conditions and generate an isomerization zone effluent.

20. The process of claim 19 wherein fractional distillation is used to perform the separating of the substantially solvent-free aliphatic hydrocarbons stream into a C$_5$-C$_7$ aliphatic hydrocarbon stream and a C$_7$-C$_8$ aliphatic hydrocarbon stream.

* * * * *